United States Patent [19]

Nielson et al.

[11] Patent Number: 4,572,008
[45] Date of Patent: Feb. 25, 1986

[54] NON-SPARKABLE SAFETY SAMPLE WEIGHT

[76] Inventors: Kimberly H. Nielson, R.R. 2, Box 229, Sullivan, Ill. 61951; Lloyd Hudson, 1216 W. Grider St., Sullivan, Ill. 61951

[21] Appl. No.: 670,498

[22] Filed: Nov. 13, 1984

[51] Int. Cl.$^4$ ............................................. G01N 1/12
[52] U.S. Cl. ................................................. 73/864.51
[58] Field of Search ........... 73/864.51, 864.63, 864.64, 73/864.74

[56] References Cited

U.S. PATENT DOCUMENTS 2,110,876  3/1938  Holman ............................ 73/864.63
2,968,184  1/1961  Archer et al. .................... 73/864.64

Primary Examiner—S. Clement Swisher
Attorney, Agent, or Firm—Stoll, Wilkie, Previto & Hoffman

[57] ABSTRACT

A combined weight and sampling device as described for use in grain elevators and similar storage facilities. The device comprises a weight element which is attached to the end of a measuring tape for being lowered to the top surface of the stored product for volume measurement purposes. Additionally, the device includes a hollow upper portion which will be filled with the measured material for sampling purposes. All of the structural elements of the device are formed of non-sparkable material, i.e. non-ferrous materials to eliminate the possibility of a spark induced explosion of grain dust, etc.

5 Claims, 5 Drawing Figures

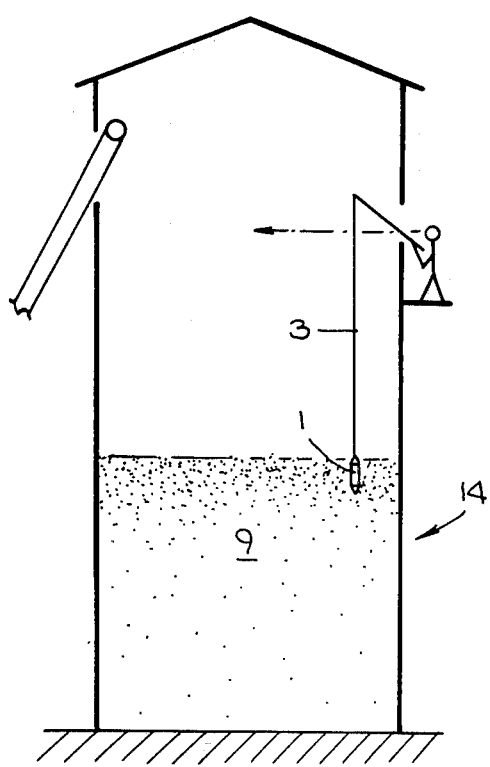
Fig. 1.
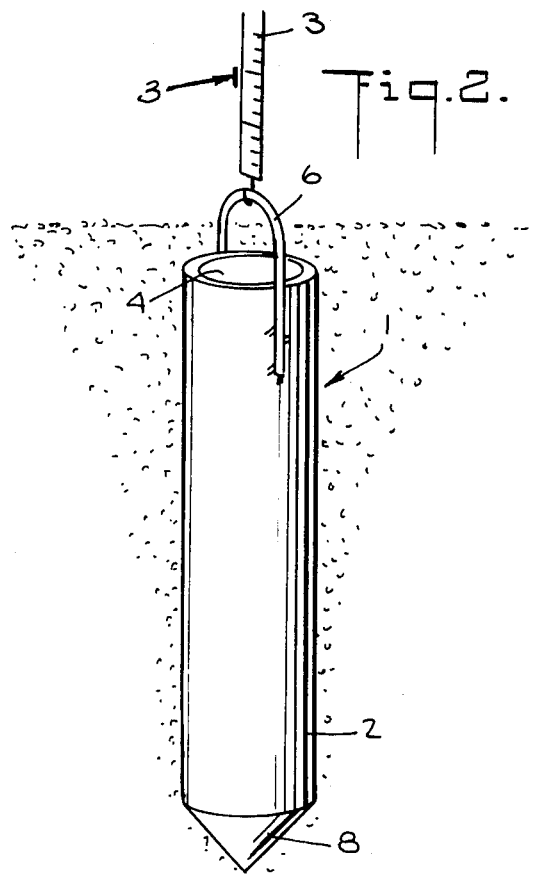
Fig. 2.
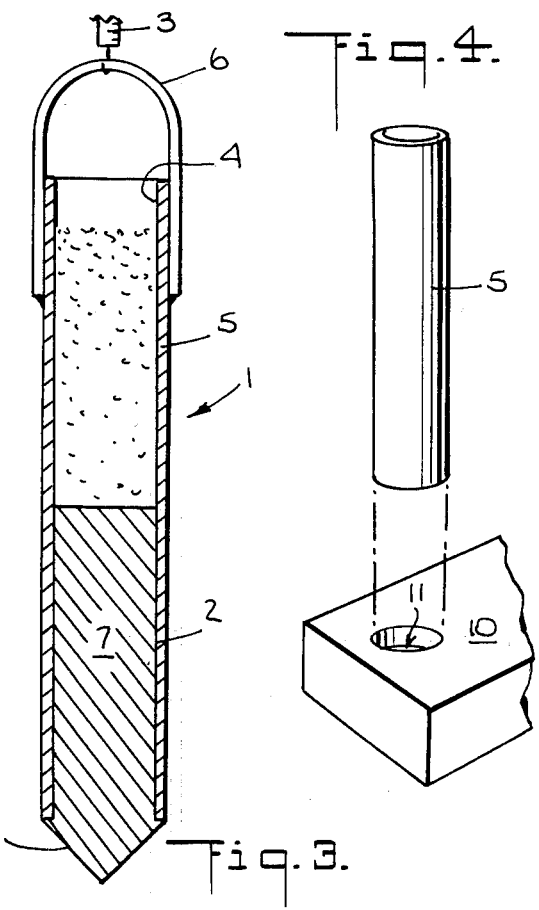
Fig. 3.
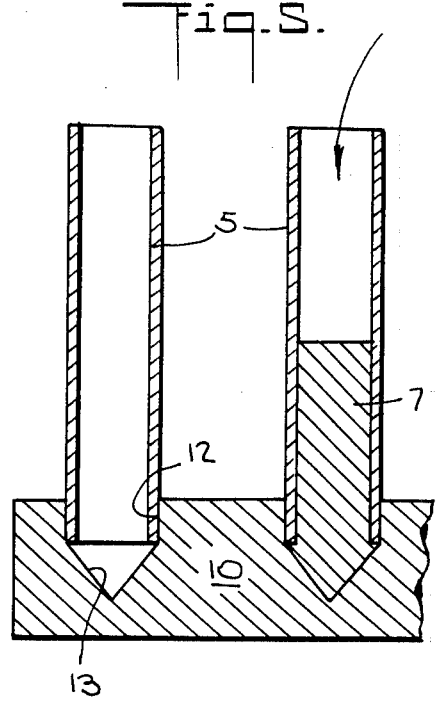
Fig. 4.
Fig. 5.

NON-SPARKABLE SAFETY SAMPLE WEIGHT

BACKGROUND OF THE INVENTION

The present invention relates to sampling and measuring operations such as are performed frequently in storage means such as grain elevators and which are accessable from their tops. It is common practice to determine the amount of grain so stored by dropping a measuring tape from the top of the elevator to the surface of the grain thereby measuring the remaining unfilled portion of the storage elevator. In present practice, it is customary to use any one of a number of convenient weights affixed to the tape end for this purpose and the most commonly available of these weights are often metallic nuts or bolts or other ferrous objects which provide a convenient size and weight. The result of this practice had been a number of fires or explosions caused by the use of such weights where their striking metallic elevator surfaces or interior machinery has created a spark igniting explosive dust accumulations. The weight of the present invention is formed with non-ferrous and non-sparkable materials on all surfaces which might possibly strike another object when dropped or thrown into the measured elevator.

In addition, the device of the present invention includes a hollow upper portion adapted to receive a sample of the grain or other product being measured so that the elevator supervisor may inspect the condition of the stored product. Such samples are presently obtained by the elevator operators climbing down into the various bins to obtain the samples.

Accordingly, an object of the present invention is to provide an improved weight for use in measurements in storage bins.

Another object of the present invention is to provide an improved device for obtaining samples of stored grain or other products.

Another object of the present invention is to provide an improved combined weight and sampling device for use in storage bins.

Another object of the present invention is to provide an improved non-sparkable safety weight and sampling device.

Another object of the present invention is to provide a relatively simple and improved weight and sampling device which is easily manufactured.

Other and further objects of the present invention will become apparent upon an understanding of the illustrative embodiments about to be described, or will be indicated in the appended claims, and various advantages not referred to herein will occur to one skilled in the art upon employment of the invention in practice.

BRIEF DESCRIPTION OF THE DRAWINGS

A preferred embodiment of the invention has been chosen for purposes of illustration and description and is shown in the accompanying drawings, forming a part of the specification, wherein:

FIG. 1 is a diagramatic view of the device of the present invention as employed in a grain storage elevator.

FIG. 2 is a perspective view of a weight and sampling device in accordance with the present invention.

FIG. 3 is a vertical sectional view of the device taken along line 3—3 on FIG. 2.

FIGS. 4 and 5 are perspective and sectional views illustrating a preferred method and means for forming the device of the present invention.

DESCRIPTION OF THE PREFERRED EMBODIMENT

A preferred embodiment of the weight and sampling device of the present invention is illustrated in the FIGURES at 1. It comprises a lower weighted portion 2 which provides the necessary weight to lower a tape measure 3 and to cause entry of the device 1 sufficiently far into stored material to obtain a sample in its upper hollow portion 4. A number of non-sparkable materials may be employed in forming the device such as lead or tin or brass or copper or other non-ferrous metals or heavier plastic materials.

The preferred embodiment illustrated comprises a hollow copper tube 5 having a connector 6 at its upper end to connect it to the measuring tape 3 and having a weighted lower portion 2 comprising a poured-in lead core 7 with a rounded or sharpened point 8 to facilitate the entry of the device 1 into the measured material 9. The tube 5 may be copper tubing having a thickness sufficient to form a rigid device or may be another material coated with copper to form a non-sparkable outer surface.

FIGS. 4 and 5 illustrate a preferred method and means for forming the weighted core 7 including the sharpened point 8. A mold 10 is illustrated having one or more cavities 11. The upper cylindrical portion 12 of the aperture 11 is dimentioned to receive the lower ends of the hollow tubes 5. The tubes 5 sit solidly in the mold 10 at the point where the mold cavities taper inwardly to form the point 8 of the weight. After the hollow tubing 5 is positioned in each of the mold cavities 11, melted lead 7 is poured into the tubes 5 to the depth desired which conveniently may be approximately half way up each hollow tube 5. The lead 7 fills this portion of the tube 5 and also flows into and solidifies within the tapered portion 13 of the mold cavities providing the points 8 for the devices 1. Other relatively heavy materials may also be melted and poured within the tube to form the weight end as long as they are non-sparking materials as discussed above.

The top of the tube 5 is provided with a loop or other connector 6 to engage the end of the tape measure 3 and is attached by any convenient means such as welding or soldering or bolting to the upper end of the tube 5.

After the above forming steps, the point 8 is sanded or filed to form a smooth penetrating surface of the desired conical shape generally as illustrated and the outer surface of the entire device 1 is cleaned and polished both to provide an attractive device and to facilitate the entry of the device into the measured product. The weight of the device, which in practice may originally have been a hollow tube about ¾ inches in diameter and six or seven inches long, when partially filled with lead provides a device which conveniently passes into the measured product at least slightly below its top end permitting the grain or other measured product to flow into the hollow sampling portion 4.

FIG. 1 illustrates the device 1 after being dropped freely into or otherwise manipulated in the storage bin 14 to assure the entry of the device 1 below the material 9 surface in a measuring and sampling operation.

It will be seen that a relatively simple but effective spark-proof weight and sampling device has been provided for inspections of grains levels and conditions in grain elevators and other storage bins. The device clearly eliminates the present dangers encountered when sparkable weights are used in such inspecting operations.

As various changes may be made in the form, construction and arrangement of the invention and without departing from the spirit and scope of the invention, and without sacrificing any of its advantages, it is to be understood that all matter herein is to be interpreted as illustrative and not in a limiting sense.

Having thus described our invention, we claim:

1. A weighted grain elevator sampling device comprising in combination:
   a tubular member having a pointed lower end and an open upper end;
   a means for weighing the member position at its bottom portion;
   a hollow grain receiving portion open to the open upper end of said tubular member;
   a coupling means at the top of said member for attaching it to a sampling line and;
   said weighting means being poured in and solidified and having a generally conical point at its lower end.

2. A weighted grain elevator sampling device comprising in combination:
   a non-ferrous member with a solid lower portion having a pointed lower end and a hollow upper portion; said solid lower portion comprising a flowed-in means for weighting the member with the pointed lower end being the bottom of said weighting means;
   said hollow portion being open to the open upper end of said member;
   a coupling means at the top of said member for attaching it to a sampling line.

3. The device as claimed in claim 2 in which said member comprises at least partially copper.

4. The device as claimed in claim 2 in which said weighting means comprises lead.

5. The device as claimed in claim 2 in which said weighting means is poured in and solidified and said pointed end is generally conical.

* * * * *